US008790872B2

(12) United States Patent
Paulie et al.

(10) Patent No.: US 8,790,872 B2
(45) Date of Patent: *Jul. 29, 2014

(54) NON-ELISPOT ASSAY

(75) Inventors: Staffan Paulie, Nacka Strand (SE); Sten Braesch-Andersen, Nacka Strand (SE)

(73) Assignee: Mabtech AB, Nacka Strand (SE)

( * ) Notice: Subject to any disclaimer, the term of this patent is extended or adjusted under 35 U.S.C. 154(b) by 908 days.

This patent is subject to a terminal disclaimer.

(21) Appl. No.: 11/587,545

(22) PCT Filed: Apr. 29, 2005

(86) PCT No.: PCT/EP2005/004620
§ 371 (c)(1),
(2), (4) Date: Aug. 17, 2007

(87) PCT Pub. No.: WO2005/106479
PCT Pub. Date: Nov. 10, 2005

(65) Prior Publication Data
US 2008/0145837 A1 Jun. 19, 2008

(30) Foreign Application Priority Data
Apr. 30, 2004 (GB) .................................. 0409775.4

(51) Int. Cl.
C12Q 1/68 (2006.01)
C12Q 1/70 (2006.01)
A61K 49/00 (2006.01)
A61K 39/00 (2006.01)
A61K 39/395 (2006.01)
A61K 39/42 (2006.01)

(52) U.S. Cl.
USPC .............. 435/6.1; 435/5; 424/9.1; 424/141.1; 424/139.1; 424/147.1; 424/159.1

(58) Field of Classification Search
None
See application file for complete search history.

(56) References Cited

U.S. PATENT DOCUMENTS

| | | | |
|---|---|---|---|
| 4,591,570 A | 5/1986 | Chang | |
| 5,432,099 A | 7/1995 | Ekins | |
| 6,410,252 B1 | 6/2002 | Lehmann et al. | |
| 2003/0021766 A1 | 1/2003 | Vajdy et al. | |
| 2004/0049351 A1 | 3/2004 | Matson et al. | |
| 2006/0079461 A1 | 4/2006 | Brewer et al. | |
| 2007/0178449 A1 | 8/2007 | Braesch-Andersen et al. | |

FOREIGN PATENT DOCUMENTS

| | | |
|---|---|---|
| EP | 0 063 810 A1 | 11/1982 |
| EP | 0 957 359 A2 | 11/1999 |
| JP | 6-502726 | 3/1994 |
| WO | WO 84/03151 A1 | 8/1984 |
| WO | WO 90/04182 A1 | 4/1990 |
| WO | WO 01/27611 A3 | 4/2001 |
| WO | WO 02/073195 A2 | 9/2002 |
| WO | WO 03/023360 A2 | 3/2003 |
| WO | WO 03/038062 A3 | 5/2003 |
| WO | WO 2005/106482 A1 | 11/2005 |

OTHER PUBLICATIONS

R&D Systems, Mouse IFN-γ Development Module product information sheet, Catalog No. SEL485, 2008.*
Chapoval, S.P., et al., "Allergic Inflammatory Response to Short Ragweed Allergenic Extract in HLA-DQ Transgenic Mice Lacking CD4 Gene," *J. Immunol.*, 168:890-899 (2002).
Chen, Y. and Peng, Z., "A Sensitive in Situ Elisa for Quantitative Measurements of Cytokines and Antibodies Secreted by Culture Lymphocytes," *J. Immunoassay & Immunochemistry* 22(4):353-369 (2001).
Come, P., et al., "Detection and Enumeration of HIV-1-Producing Cells by ELISPOT (Enzyme-Linked ImmunoSpot) Assay," *J. Acquired Immune Deficiency Syndromes and Human Retrovirology* 20(5):442-447 (1999).
Czerkinsky, C.C., et al., "An Immunoenzyme Procedure for Enumerating Fibronectin-Secreting Cells," *J. Immunoassay* 5(3&4):291-302 (1984).
Ekins, R.P. and Chu, F., "Developing Multianalyte Assays," *Trends in Biotechnology* 12:89-94 (1994).
Gazagne, A., et al., "A Fluorospot Assay to Detect Single T Lymphocytes Simultaneously Producing Multiple Cytokines," *J. Immunol. Methods* 283:91-98 (2003).
Geppert, T.D and Lipsky, P.E., "Accessory Cell Independent Proliferation of Human T4 Cells Stimulated by Immobilized Monoclonal Antibodies to CD3," *J. Immunol.*, 138(6):1660-1666 (1987).
Hagiwara, E., et al., "Phenotype and Frequency of Cells Secreting IL-2, IL-4, IL-6, IL-10, IFN and TNF-α in Human Peripheral Blood," *Cytokine* 7(8):815-822 (1995).
Jansson, A., et al., "Elispot Assay Detection of Cytokine Secretion in Multiple Sclerosis Patients Treated with Interferon-β1a or Glatiramer Acetate Compared With Untreated Patients," *Multiple Sclerosis* 9:440-445 (2003).
Kouwenhoven, M., et al., "Enzyme-Linked Immunospot Assays Provide a Sensitive Tool for Detection of Cytokine Secretion by Monocytes," *Clin. Diag. Lab. Immunol.*, 8(6):1248-1257 (2001).
Mäkitalo, B., et al., "ELISpot and ELISA Analysis of Spontaneous, Mitogen-induced and Antigen-specific Cytokine Production in Cynomolgus and Rhesus Macaques," *J. Immunol. Methods* 270:85-97 (2002).
Moldovan, I.R., et al., "Interferon Gamma Responses to Myelin Peptides in Multiple Sclerosis Correlate with a New Clinical Measure of Disease Progression," *J. Neuroimmunology* 141:132-140 (2003).
Okamoto, Y., et al., "Development of a Dual Color Enzyme-linked Immunospot Assay for Simultaneous Detection of Murine T Helper Type 1-and T Helper Type 2-Cells," *Immunopharmacology* 39:107-116 (1998).

(Continued)

*Primary Examiner* — Benjamin P Blumel
(74) *Attorney, Agent, or Firm* — Hamilton, Brook, Smith & Reynolds, P.C.

(57) ABSTRACT

A method of detecting the production of an analyte by cells in a sample, which method comprises: (i) providing an antibody capable of binding to said analyte and a first agent capable of enhancing detection of said analyte, wherein said antibody and said first agent are immobilized on the same support; (ii) contacting said antibody and said agent with a sample of cells; and (iii) detecting binding of said analyte to said antibody thereby detecting the production of an analyte by cells in a sample.

37 Claims, No Drawings

(56) References Cited

OTHER PUBLICATIONS van Emmerik, N.E.M., et al., "The Avidity of Allospecific Cytotoxic T Lymphocytes (CTL) Determines Their Cytokine Production Profile," *Clin. Exp. Immunol.*, 110:447-453 (1997).

Culshaw, R.J., et al., "Gut Intraepithelial Lymphocytes Induce Immunity against Cryptosporidium Infection Through a Mechanism Involving Gamma Interferon Production." Infection and Immunity, pp. 3074-3079 (Aug. 1997).

Ott, P.A., et al., "CD28 Costimulation Enhances the Sensitivity of the ELISPOT Assay for detection of Antigen-Specific Memory Effector CD4 and CD8 Cell Populations in Human Diseases." Journal of Immunological Methods, vol. 285, pp. 223-235 (Feb. 2004).

Jennes, W., "Enhanced ELISPOT Detection of Antigen-Specific T Cell Responses from Cryopreserved Specimens with Addition of Both IL-7 and IL-15—the Amplispot Assay." Journal of Immunological Methods, vol. 270, pp. 99-108 (2002).

Westermann, J., et al., "T Cell Reactivity Against bcr/abl Fusion Peptides in Healthy Donors and CML Patients", [online], Chemical Abstracts Service, (Dec. 2002).

Crotty, et al., "Tracking human antigen-specific memory B cells: a sensitive and generalized ELISPOT system," *J. of Immunological Methods*, 286: 111-122 (2004).

Okamoto, et al., "Cytokine Balance in the Pathogenesis of Rheumatoid Arthritis," *Yakugaku Zasshi*, 121(2): 131-138 (2001).

Hassan, T., et al., "Expression of a Unique Protein on Colon Cancer Cells that Reacts with a Novel Monoclonal Antibody and Ulcerative Colitis Serum," *Clin. Exp. Immunol.*, 100:457-462 (1995).

Helms, T., et al., "Direct Visualization of Cytokine-Producing Recall Antigen-Specific CD4 Memory T Cells in Healthy Individuals and HIV Patients," *The Journal of Immunology*, 164:3723-3732 (2000).

Huang, R., et al., "Enhanced Protein Profiling Arrays with ELISA-Based Amplification for High-Throughput Molecular Changes of Tumor Patients' Plasma," *Clinical Cancer Research*, 10:598-609 (Jan. 2004).

Nicolaieff, A., et al., "Detection of Rotavirus by Serological Trapping on Antibody-Coated Electron Microscope Grids," *Journal of Clinical Microbiology*, 12(1):101-104 (Jul. 1980).

Notification of Transmittal of the International Search Report and the Written Opinion of the International Searching Authority, or the Declaration, International Search Report and the Written Opinion in PCT Application No. PCT/EP2005/004620, 14 pages, mailed Sep. 26, 2005.

Notification Concerning Transmittal of International Preliminary Report on Patentability and International Preliminary Report on Patentability in International Application No. PCT/EP2005/004620, 9 pages, mailed Nov. 9, 2006.

Butler, J.E., "Solid Supports in Enzyme-Linked Immunosorbent Assay and Other Solid-Phase Immunoassays," *Methods*, 22:4-23 (2000).

U.S. Appl. No. 11/587,350, filed Mar. 14, 2011, Office Action.

Notice of Allowance dated Aug. 26, 2013 in U.S. Appl. No. 11/587,350, entitled "Cultispot Assay."

* cited by examiner

NON-ELISPOT ASSAY

RELATED APPLICATIONS

This application is the U.S. National Stage of International Application No. PCT/EP2005/004620, filed Apr. 29, 2005, published in English, and claims priority under 35 U.S.C. §119 or 365 to UK Application No. 0409775.4 filed Apr. 30, 2004.

FIELD OF THE INVENTION

The invention relates to a method for detecting production of an analyte by a sample of cells, an assay plate for use in the method and a kit comprising the assay plate.

BACKGROUND TO THE INVENTION

The enzyme-linked immunospot assay (ELISpot) is widely used for the detection of T-cell specific responses. In the ELISpot assay, T-cells secreting a specific cytokine are detected by incubating the T-cells in an ELISpot assay plate on which antibodies specific for the cytokine are immobilised. Cytokine bound to the antibodies can then be visualised using standard immunoassay procedures. Spots of bound cytokine localised in areas of the assay plate where cytokine production has occurred indicate the presence of activated T-cells. Since each spot represents cytokine production by a single cell, if the number of cells present in the assay plate are known, the frequency of responding cells can be ascertained by counting the number of spots formed.

The ELISpot assay has also been used for other purposes such as the detection of virus infected cells, the enumeration of cells secreting specific antibody, the detection of cells secreting fibronectin and the study of monocytes.

The use of soluble cofactors to enhance the detection of positive cells in the ELISpot assay has been described. Immobilised cofactors have been used to stimulate T-cells and the presence of cytokines in the culture medium has subsequently been detected by ELISA-based analysis.

SUMMARY OF THE INVENTION

The present invention provides an improved ELISpot assay in which the detection of cells secreting an analyte is enhanced by the use of a bioactive molecule. The assay of the invention utilises an assay plate on which the specific binding agent for the analyte is immobilised on the same surface as the bioactive molecule. The bioactive molecule serves to potentiate the secretion of the analyte in response to a specific stimulus. The bioactive molecule thus serves to enhance detection of cells which secrete the analyte. This potentiating effect may be manifested as a higher number of specific spots resulting from more effective stimulation of all potentially responding cells in a sample. Alternatively, the potentiating effect may be manifested in more distinct spots resulting from higher production of the analyte by the individual cells during the course of the assay. For example, the cells may be more effectively stimulated so that production of the analyte is initiated at an earlier time point. The assay of the invention is useful both as a research tool and as a diagnostic tool.

Accordingly, the present invention provides:
a method of detecting the production of an analyte by cells in a sample, which method comprises:
(i) providing an antibody capable of binding to said analyte and a first agent capable of enhancing detection of said analyte, wherein said antibody and said first agent are immobilised on the same support;
(ii) contacting said antibody and said agent with a sample of cells; and
(iii) detecting binding of said analyte to said antibody thereby detecting the production of an analyte by cells in a sample;
an assay plate for use in a method of the invention comprising an antibody specific for an analyte and a first agent capable of enhancing detection of cells secreting said analyte, wherein said antibody and said first agent are immobilised on the same surface;
a kit comprising an assay plate of the invention and a detection means; and
use of an assay plate or kit of the invention to monitor an immune response, to diagnose viral infection in vitro or to identify antiviral drugs.

DETAILED DESCRIPTION OF THE INVENTION

The present invention provides an in vitro of detecting the production of an analyte by cells in a sample, which method comprises:
(i) providing an antibody capable of binding to said analyte and a first agent capable of enhancing detection of said analyte, wherein said antibody and said first agent are immobilised on the same support;
(ii) contacting said antibody and said agent with a sample of cells; and
(iii) detecting binding of said analyte to said antibody thereby detecting the production of an analyte by cells in a sample.

The method of the invention is effectively an ELISpot assay in which an agent capable of enhancing detection of positive cells is immobilised on the same support as the antibody used for detection. The use of agents to enhance detection of cells in the EILSpot assay have been described previously. However, such agents had not previously been immobilised in the same wells as the antibodies used for detection but have been added to the assay in soluble form.

By providing both an agent capable of enhancing detection and an antibody on the same support the assay is much simpler because the number of additions required is reduced. This is particularly important where the assay is used for large scale screening, for example, in diagnostic applications, where simplicity and safety are essential.

In addition, the agent may be more effective if administered in an immobilised form. For example, receptors on T-cells are often dependent on being cross-linked in order to be able to transmit their signal and such cross-linking may be achieved more effectively if the stimulatory agent is immobilised. In a particular embodiment of the invention, where the agent capable of enhancing detection is an antibody to a molecule that stimulates spontaneous secretion of the analyte, the antibody need not have "neutralising" capacity as would be required if the antibody were added in solution.

In an assay of the invention, the presence of the immobilised agent capable of enhancing detection serves to compensate for the incomplete activation process observed standard in ELISpot assays. As a consequence of this compensation, an increased number of spots may be achieved in an assay of the invention and hence a more accurate estimation of the frequency of cells with the capacity to respond to an agent capable of stimulating an analyte may be made.

Cells

In one preferred embodiment, the cells are T-cells. The T-cells are generally taken from the subject in a blood sample, although other types of sample which contain T-cells can be used. The sample may be added directly to the assay or may be processed. Typically, the processing may comprise the isolation of cells from the blood and the suspension of these in cell culture medium or buffer. The cell suspension may be diluted to contain different concentrations of cells depending on the test situation. The concentration of cells in the sample may be higher than that in blood.

Preferably, the T-cells used in the assay are in the form of unprocessed or diluted samples. The T-cells may be freshly isolated (e.g. freshly isolated mononuclear cells (MCs) or peripheral blood mononuclear cells (PBMCs)) which are used directly ex vivo, i.e. they are not cultured before being used in the method. Alternatively, the T-cells may have been cultured in vitro prior to use in the assay.

In a 96 well plate format assay, generally from about $2.5 \times 10^4$ to about $3 \times 10^5$ cells are added to each well. In a typical 96-well plate format assay for analysing specific responses, from about $10^5$ to about $3 \times 10^5$ cells may be added to each well. Cell numbers over about $3 \times 10^5$ cells in the 96-well plate format may result in multiple cell layers which in turn may result in more diffuse spots. If it is wished to investigate more cells, the number of wells should be increased or plates with larger wells should be used. For specific stimulation of PBMC, the optimal cell concentration is from about $2 \times 10^5$ to about $3 \times 10^5$ cells. For polyclonal stimulations with, for example PHA or anti-CD3, cell numbers need to be significantly lower, for example from about $2.5 \times 10^4$ to about $5 \times 10^4$ cells/well as otherwise production by too many cells will result in an inability to see the individually producing cells. If using enriched positive cells (e.g. isolated T-cell clones), lower cell numbers are also preferred.

In a second embodiment the cells may be virus infected cells. The cells may be blood cells, for example lymphocytes, monocytes or granulocytes. Other suitable cells may be isolated from urine, saliva, semen or vaginal secretions. Other cell types may also be screened, depending on the tropism of the virus. Viral infected cells that may be detected by a method of the invention include cells infected with human immuno-deficiency virus (HIV), Epstein Barr virus (EBV) and cytomegolovirus (CMV).

In other embodiments of the invention, the cells may be, for example, parasite infected cells, such as blood cells, bacterial infected cells, insulin producing islet cells, dendritic cells, cancer cells or neuronal stem cells.

Analyte

The analyte is typically an immunoreactive substance, typically a protein. In the embodiment where the cells are T-cells, the analyte is typically one or more cytokine. The cytokine may be selected from an interleukin, such as IL-1, IL-2, IL-4, IL-5, IL-6, IL-10, IL-12 or IL-13, an interferon, such as IFN-γ or IFN-α, other cytokines, such as TNF-α, perforin or granzyme. Preferably the cytokine is IFN-γ or IL-4. Typically, the one or more cytokine is released when the T-cell is contacted with a stimulatory substance such as an antigen or allergen. A method of the invention may detect one, two, three or more analytes simultaneously or sequentially. Preferred combinations of cytokines for simultaneous detection include IFN-γ and any one of IL-2, IL-4, IL-5 and IL-10.

In the embodiment where the cells are virus infected cells, the analyte is typically a virus particle or virus protein. Examples of virus particles and proteins that can be detected include Epstein-Barr virus and human immunodeficiency virus types I and II (HIV).

Where the cells are cancer cells, the analyte is typically a growth factor or growth regulatory protein. Where the cells are parasite infected cells, such as parasite infected blood cells, the analyte is typically a parasite derived protein.

Antibody

The antibody is capable of binding, preferably specifically binding, to the analyte. The antibody may be replaced by any specific binding agent capable of specifically binding to the analyte. An agent or antibody "specifically binds" to a substance when it binds with preferential or high affinity to the substance for which it is specific but does not bind, does not substantially bind or binds with only low affinity to other substances. The antibody may be a monoclonal or a polyclonal antibody. Monoclonal antibodies are preferred for use in a method of invention.

The antibody may be a monoclonal or polyclonal antibody. Monoclonal antibodies are preferred. The antibody may also be, or comprise, an affinity ligand or an antibody fragment, which fragment is capable of binding to the analyte. Such antibody fragments include Fv, F(ab') and F(ab')$_2$ fragments as well as single chain antibodies.

A method of the invention may utilise one or more, for example two, three, or four antibodies, wherein each antibody specifically binds to a different analyte.

In one embodiment, the invention provides a method of detecting T-cells which secrete a cytokine in response to a stimulatory agent. In this embodiment, an antibody suitable for use in the method of the invention typically binds specifically to one or more cytokines, for example to two, three or four cytokines but preferably to one cytokine. Preferably the antibody binds specifically to IFN-γ or IL-4. Antibodies to cytokines are commercially available, or can be made using standard techniques. Commercially available antibodies include the following monoclonal antibodies from Mabtech AB, Stockholm, Sweden: IL2-I and IL2-II for IL-2, 82.4 and 12.1 or IL4-I and IL4-II for IL-4, TRFK5 and 5A10 for IL-5, IL13-I and IL13-2 for IL-13, 1-D1K and 7-B6-1 for IFN-γ, 13A5 and 39C3 for IL-6, 9D7 and 12G8 for IL-10, IL-12-I, IL-12-II and IL-12-III for IL-12, TNFα-I and TNFα-II for TNF-α, pf-344 for perforin and IFNα-I and IFNα-II for IFNα.

In a second embodiment, the invention provides a method of detecting virus infected cells. In this embodiment, the antibody typically binds to a virus particle or a virus protein. Preferably the antibody binds specifically to the virus envelope or to a viral protein secreted by infected cells.

Agent Capable of Enhancing Detection of Cells

The agent capable of enhancing detection of cells which secrete an analyte may be a substance that enhances secretion of said analyte. Such agents are useful as positive controls. Therefore, such a method of the invention may be carried out at the same time as a method in which no agent capable of enhancing detection is used. In this aspect, one or more but not all of the wells in a microtiter plate may contain the agent capable of enhancing detection in addition to the antibody specific for the analyte. In this embodiment of the invention, the agent capable of enhancing detection of cells may be a polyclonal activator such as an antibody to CD3 or a lectin such as phytohaemagglutinin (PHA) or convanavalin A (ConA). These activators may be useful in enhancing detection of activated T-cells.

The agent capable of enhancing detection of cells which secrete the analyte may act to potentiate specific secretion of the analyte in response to an agent that stimulates secretion of the analyte. The agent capable of enhancing detection may, therefore, provide a co-stimulatory signal for secretion of the analyte.

In the embodiment for detecting activated T-cells, the agent may be an antibody or recombinant ligand to a co-stimulatory molecule such as CD28, inducible co-stimulatory (ICOS) molecule or CD40. The processes of antigen presentation and the cell-to-cell contacts which are important for an immune response are not optimally met under normal in vitro conditions provided in the ELISpot assay. The provision of a co-stimulatory signal in the ELISpot plate substitutes for the signals normally provided in the cell-to-cell contacts and thus enhances the number of responding cells in a specific manner. The results shown in Table 2 demonstrate that the use of immobilised anti-CD28 antibodies significantly enhances the specific responses of T-cells to the antigens purified protein derivative (PPD) and tetanus toxin (TT).

Another example of agents which potentiate secretion of an analyte in response to a stimulatory agent are growth factors, such as IL-2 and IL-15. These growth factors act to potentiate specific immune responses providing the responding T-cells with further signals for activation. Other examples of suitable agents to potentiate a stimulatory signal are IL-4 which further potentiates the stimulation of IL-4 producing cells and IL-12 that may be used to promote the production of Th-1 cytokines such as interferon-γ (IFN-γ).

The agent capable of enhancing detection of cells which secrete an analyte may act by inhibiting a signal which inhibits secretion of the analyte. For example, in the embodiment for the detection of T-cells the agent may be an antibody to a generally immunoinhibitory molecule such as IL-10 or TGF-β. Antibodies to generally immunoinhibitory molecules will "absorb" the immunoinhibitory molecules to the well surface, thereby making the immunohibitory molecules less accessible to the potentially responding T-cells.

In another alternative, the agent capable of enhancing detection of cells which secrete the analyte may act to inhibit a stimulatory signal in order to suppress spontaneous secretion of the analyte. This may help to make the specific responses more easily revealed by improving the signal to noise ratio. For example Granzyme B and IFN-γ are both produced by natural killer (NK) cells as well as by T-cells. The agent may suppress the spontaneous production of Granzyme B or IFN-γ from NK cells in order to aid detection of Granzyme B or IFN-γ from T-cells. Suitable agents that act in this way include antibodies specific for a molecule that acts as a stimulatory signal.

Extra-cellular matrix proteins such as fibronectin and laminin are further examples of agents capable of enhancing detection of an analyte by potentiating secretion of the substance in response to a stimulatory signal. Extra-cellular matrix proteins are essential for the proper interaction of matrix-dependent cellular modulators, such as chemokines, with immune cells. Inclusion of extracellular matrix proteins may, therefore, be required to provide optimal conditions for stimulation.

In a method of the invention one, two, three or more, for example four or five, agents capable of enhancing detection may be bound to the support. Where two or more such agents are bound to the support, the agents may act by the same or different mechanisms and may enhance the detection of the same or different analyte. For example, where the cells are T-cells, two costimulatory signals may be used to optimally detect both CD4 and CD8 responding cells. Here, the detection system is preferably based on more than one cytokine, such as IL-4 and IFN-γ which are usually produced by separate sets of T-cells.

In the embodiment of the invention for detecting virus infected cells, the agent capable of enhancing detection of such cells is preferably an agent capable of activating virus replication. In the case of, for example HIV, the activator of viral replication may be a polyclonal activator such as anti-CD3 or PHA which both activate virus replication in T-cells.

Agent Capable of Stimulating Production of Analyte

The method of the invention is typically used to detect cells which produce an analyte in response to a specific stimulatory signal. Accordingly, the cells being tested may be contacted with an agent capable of stimulating productions, for example, secretion of the analyte prior to contacting the cells with the antibody and agent capable of enhancing detection on the support. Alternatively or additionally, the cells may be contacted with the agent capable of stimulating production of the analyte at the same time as the immobilised agent capable of enhancing detection and the immobilised antibody. Preferably, the cells being tested are contacted with the agent capable of stimulating production at the same time as the agent capable of enhancing detection and the antibody. Where the cells are T-cells it is particularly preferred that the agent capable of stimulating production is added to the assay wells, i.e. that the T-cells are simultaneously brought into contact with the agent capable of stimulating production, the agent capable of enhancing detection and the antibody. The agent capable of stimulating production of the analyte may be present in solution or immobilised on the support.

In the embodiment where the method is for detecting activated T-cells, the agent capable of stimulating secretion is typically an antigen. The antigen may be from a pathogen such as a virus or bacteria. The antigen may be associated with an autoimmune disorder, such as autoimmune neurological disorders (myelin) or diabetes (glutamic acid decarboxylase (GAD)). The antigen may be a tumour antigen or an allergen. The agent capable of stimulating secretion may comprise a crude antigenic mixture isolated or recombinantly produced protein(s) and/or manufactured peptides.

Agent Capable of Inhibiting Secretion of Said Analyte

The method of the invention may be used to detect cells which secrete an analyte, either spontaneously or in response to a stimulatory signal. The method of the invention may also be used to identify an agent which inhibits secretion of the analyte. Such an agent may inhibit the spontaneous secretion of the substance or may inhibit secretion of the substance in response to a specific stimulus.

For example, in the embodiment of the invention for detecting virus infected cells, the method may be used to identify anti-viral drugs. In such a method of drug screening, the method of the invention may be carried out in the presence and absence of the agent being tested and any decrease in the number of cells secreting a viral protein or particle in the presence of the test agent indicates that the agent may be useful as an anti-viral drug.

In the embodiment of the invention for detecting T-cells, the method may be used to identify immunoregulatory agents, for example in an antigen-specific system. The immunoregulatory agents may be suppressive or potentiating. In such a method of screening, the method of the invention may be carried out in the presence and absence of the test agent and any increase or decrease in the number of cells secreting a cytokine in the presence of the test agent indicates that the agent has immunoregulatory activity.

The cells may be incubated with the test agent prior to contacting the cells with the antibody and agent capable of enhancing detection. Alternatively, the test agent may be contacted with the cells at the same time as the cells are brought into contact with the antibody and agent capable of enhancing detection.

Suitable Assay Format

The cells and agent capable of stimulating secretion of said analyte of the cells and a test agent may be contacted under any conditions suitable for stimulation of secretion. The conditions may also be suitable for the analyte to interact directly with the immobilised antibodies. Generally, the cells will be present in a liquid sample. The stimulatory agent or test agent may be immobilised to the surface to which the antibody and agent capable of enhancing detection are immobilised. Cells may then be brought into contact with the stimulatory agent or test agent, the antibody and the agent capable of enhancing detection simultaneously.

The assay may be carried out in any suitable volume. Typical volumes of the cell sample range from about 10 µl to about 1 ml, for example from about 25 µL to about 250 µl, from about 30 µl to about 200 µl from about 40 µl to about 150µ or about 50 µl to about 100 µl. Typically, the length of time for which the cells are incubated with the antibody and agent capable of enhancing detection is from about 4 to about 50 hours, for example from about 6 to 48 hours from about 8 to 45 hours, from about 12 to 36 hours or from about 16 to 32 hours, preferably from about 6 to 16 hours, for example overnight.

The cells may be incubated with the antibody and agent capable of enhancing detection at any suitable temperature. The suitable temperature is in the same range as the normal body temperature of the human or animal from which the cells are derived. Typically, the incubation is carried out at a temperature between about 35° C. and about 39° C., preferably from about 36° C. to about 38° C., more preferably at about 37° C.

Detection of Antibody/Analyte Complex

The complex formed between the immobilised antibody and analyte released from the cells may be detected by any suitable means. After binding to the antibody, the analyte will remain in the vicinity of the cell which secreted it. Thus "spots" of analyte/antibody complex are formed on the support, each spot representing a cell which is secreting the substance. Quantifying the spots, and typically comparing against a control, allows cells secreting the analyte to be detected. The surface to which the antibody is immobilised is generally washed, for example in PBS, to remove unbound analyte prior to detection.

Typically the antibody/analyte complex may be detected using a second antibody which will bind to the complex. The second antibody is typically a different antibody to the first antibody. Typically, the second antibody binds the analyte at a site which is different to the site which binds the first antibody. The second antibody may bind to the complex formed between the analyte and the first antibody immobilised on the solid support.

Generally, the second antibody is labelled with a label that may be detected either directly or indirectly. A specific binding agent comprising a directly detectable label may comprise a fluorescent label such as fluoroscein, Texas red, rhodamine or Oregon green. The binding of the second fluorescently labelled antibody to the immobilised first antibody/substance complexes may be detected by microscopy. For example, using a fluorescent or bifocal microscope.

Preferably, the second antibody is conjugated to a label that may be detected indirectly. The label that may be detected indirectly may comprise an enzyme which acts on a precipitating non-fluorescent substrate that can be detected under a conventional low-magnifying, for example 10 times magnification, 20 times magnification or 50 times magnification, microscope such as a stereomicroscope. Preferably, the precipitated non-fluorescent microscope is detected using an automated ELISpot reader. An automated ELISpot reader is typically based on a video camera and image analysis software adapted for the analysis of spots. Alternatively, the spots may be detected by eye using a magnifying glass. Preferred enzymes include alkaline phosphatase and horseradish peroxidase.

A second antibody comprising an indirectly detectable label may be detected by a third antibody which is labelled directly or indirectly by a detectable label. The third antibody may typically bind to the label on the second antibody. For example, the second antibody may preferably comprise a biotin moiety, allowing detection by a third agent which comprises a streptavidin moiety and typically alkaline phosphatase or horse radish peroxidase as the detectable agent.

The second antibody may be an antibody from a different species to both the first antibody and the subject from which the cells are taken. The third binding agent may then be an antibody that specifically recognises protein from the species from which the second antibody is derived.

In all detection steps, it is desirable to include an agent to minimise non-specific binding of the second and subsequent agent. For example bovine serum albumin (BSA) or foetal calf serum (FCS) may be used to block non-specific binding.

The substance released from the cells in response to a stimulatory agent may also be released spontaneously from the cells in the absence of the agent. Therefore, it may be necessary to carry out one or more negative control assays to determine whether or not more cell is releasing the substance in response to the stimulatory agent. For example, the assay may be carried out in the absence of the stimulatory agent and the number of spots detected in the absence of the stimulatory agent may be subtracted from the number of spots (positive cells) detected in the presence of the stimulatory agent.

Assay Plate

The invention also provides an assay plate for use in a method of the invention comprising an antibody specific for an analyte that may be produced by a cell and a first agent capable of enhancing detection of cells secreting said analyte, wherein said antibody and said first agent are immobilised on the same surface.

The antibody and the first agent may be present uniformly across the support, i.e. both the antibody and first agent may be present in the same area.

Alternatively, the antibody and the first agent may be localised at discrete locations on the assay plate. Hence, in one embodiment of the invention, the antibody is coated on only a part of the support, i.e. a fraction of the surface of the support, and the first agent is coated either uniformly on the support, i.e. on the part of the support coated with the antibody and the part of the support not coated with the antibody, or only on the part of the support not coated with the antibody. In this embodiment the fraction of the support coated with the antibody may comprise from about 1/200 to about 1/2 of the total surface area, for example from about 1/100 to about 1/3, about 1/50 to about 1/4, about 1/20 to about 1/8 or about 1/10 to about 1/9 of the total surface area.

In this embodiment, a positive assay will result in the production of a spot at the site coated with the antibody. These spots are bigger than the cellular imprints seen in the regular ELISpot and so can be easily recorded by visual inspection. An image analyser may also be used, for example to provide information about spot intensity, thus giving semiquantitative information about how much cytokine is produced. This also makes it possible to identify positive responses in situations where spontaneous production of the analyte occurs in negative control wells. The fact that the cytokine is captured and detected at a limited area makes the assay very sensitive. For example, it is possible to detect T-cell responses to individual peptides which in the ELISpot assay would produce 10 spots or fewer.

In this embodiment, it is possible to simultaneously detect one or more analyte in a single well by immobilising 2 or more, for example 3, 4, 5, 6, 7, 8, 9 or 10 antibodies at discrete locations on the base of the well. The antibodies and agents are typically located on the solid surface such that a sample of cells may simultaneously contact each of the antibodies and agents on the solid surface.

The discrete location typically comprises a spot. The spot has a typical diameter of from about 1 mm to about 200 µm, for example from about 1 µm to about 100 µm or from about 10 µm to about 50 µm. From 2 to 50, from 3 to 40, from 4 to 30, from 5 to 20, from 6 to 15, from 7 to 12, 8, 9 or 10 spots of immobilized binding proteins may be present on the solid surface.

The spots may be arranged in any suitable array on the surface provided that the spots are separated from one another. The spots are typically arranged in one or more straight lines to aid identification of spots to which the first, second or further analyte has bound. For example, the spots may be arranged as a grid. In a grid, a first antibody may be present in one row or column and a second antibody or an agent in a second row or column. One or more further antibody or agent may be present in additional spots which may form additional rows or columns in the grid. Alternatively, the spots may form a circular array on the solid surface.

The antibody and agent capable of enhancing detection of cells secreting an analyte to which the antibody binds are immobilised on a solid support. Any suitable solid support may be used. The surface to which the antibody is attached may be a surface of the well, preferably the base of the well. Typically the well is present in a plate with wells, such as a microtiter plate. Separate assays can then be carried out in separate wells in the plate. Preferably the microtiter plate is a 96-well ELISpot plate. Preferably the surface to which the antibody and agent capable of enhancing detection of cells are immobilised is the base of a well. Preferably the surface is a polyvinylidene fluoride (PVDF)-membrane or a nitrocellulose membrane. Other membranes with the equivalent protein binding capacities as PVDF and nitrocellulose-membranes may also be used. Typically, the surface has a protein binding capacity of from about 50 to about 100 µg/well of a 96-well ELISpot plate, such as about 60, about 70, about 80 or about 90 micrograms per well. The surface area of a 96-well ELISpot plate is 0.32 cm$^2$. The protein binding capacity is typically from about 150 µg/cm$^2$ to about 315 µg/cm$^2$, such as about 180 µg/cm$^2$, about 200 µg/cm$^2$, about 250 µg/cm$^2$ or about 300 µg/cm$^2$.

An antibody may be bound to the support by contacting the support and antibody under conditions suitable for the antibody to bind to the support and washing to remove unbound antibodies. Similarly, the agent capable of enhancing detection of cells secreting the analyte may be bound to the support by contacting the support and the agent under conditions suitable for the agent to bind to the support and washing to remove unbound agent.

Kits

The invention also provides a kit for carrying out a method of the invention, which kit comprises an assay plate according to the invention and a means to detect binding of said analyte to said antibody.

The kit may also comprise a means to detect the substance/antibody complex. The antibody bound to the substance may be detected directly, if the antibody is directly or indirectly labelled for detection. Alternatively, a second antibody directly or indirectly labelled for detection may be allowed to bind the substance/antibody complex to allow the determination of spots. As discussed above, the second antibody may be specific for the substance, but may bind a different site on the substance from the first antibody.

The kit may additionally comprise medium for the cells, detection agents or washing buffers to be used in the detection steps.

The kit may also comprise controls, such as positive or negative controls. The method may act as a positive control to allow the detection system in the absence of the agent capable of enhancing detection to be tested.

The kit may also comprise a means to take a sample containing cells from a subject, such as a blood sample. The kit may comprise a means to separate mononuclear cells or T-cells from a blood sample.

Uses

The method of the invention may be used in research situations as well as in diagnostic applications. The method of the invention may be used in any known application of the ELISpot assay. The method of the invention may, in particular, be used in research to investigate specific immune responses, for example in vaccine studies. The method of the invention may be used in diagnostic assays aimed at detecting T-cell responses to various infectious diseases, allergens, tumour antigens or autoimmune targets.

The method of the invention provides an improved ELISpot assay. An assay carried out according to the method of the invention is more sensitive than the known ELISpot assay. The potentiating effect of the agent capable of enhancing detection of positive cells may be manifested as a higher number of specific spots (resulting from more effective stimulation of all potentially responding cells in a sample) or in more distinct spots (resulting from higher production of the analyte by the individual cells).

The method of the invention has particular utility in drug screening, for example, in identifying anti-viral drugs and immunomodulatory agents.

The method of the invention may also be used to detect responses of a variety of isolated cells. For example, insulin producing islets isolated for transplantation could be monitored for insulin production and stress responses, dendritic cells isolated for immune therapy could be monitored for responsiveness and maturation markers and neuronal stem cells isolated for stroke therapy could be monitored for stress proteins and neuronal chemotactic factors.

EXAMPLES

Methods

Preparation of Plates

PVDF membrane plates (e.g. ELIIP10SSP from Millipore, USA) are preactivated by adding 150 µl of 70% EtOH. After incubation for approximately 2 min the plate is washed with sterile water (5×200 µg/well).

Solutions of anti-cytokine-mab (e.g. the anti-IL-4 mAb, IL4-I, Mabtech AB, Sweden, 30 µg/ml) and costimulatory antibody (e.g. anti-CD-28) are prepared by diluting them in sterile PBS. For anti-CD28 a suitable concentration may be 1 to 5 µg/ml but this may vary for different antibodies and should be determined by titration. 50 µl/well of the anti-cytokine mAb is added followed by the addition of 50 µl/well of the costimulatory antibody or 50 µl/well of only PBS or the same concentration of an irrelevant mAb (the two last wells serving as controls). The plates may be wrapped in aluminium foil and stored in a refrigerator overnight.

Plates are washed 5-6 times with 200 µl of sterile PBS to remove any unbound reagents. 200 µl medium/well (RPMI 1640 medium supplemented with 10% FCS, 10 mM Hepes, 100 U/ml Penicillin-Streptomycin and 2 mM Glutamine) is added and the mixture incubated for at least 1 hour.

Cell Preparation

Freshly prepared or frozen PBMC (peripheral blood mononuclear cells) may be used for the assay (PBMC are prepared according to a standard protocol). If frozen cells are used, they are thawed in a 37° C. waterbath until a small ice crystal is left in the tube. About 0.5 ml of medium is added to the cryotube, the cells are gently suspended and transferred to a 14 ml-tube. Medium is slowly added to the cells until a volume of 12-14 ml is obtained. After centrifuging for 10 min at 900 rpm, the supernatant is removed with a pipette. The cells are suspended in medium (a sample is taken out for counting) and centrifuged a second time. The supernatant is removed and the cells are suspended in an appropriate volume of medium.

Setting Up the Assay

Cells are tested for responses to specific antigens (e.g. PPD and TT, Statens Serum Institute, Denmark; both diluted in medium and typically used at a concentration of 10 µg/ml) in the presence or absence of costimulatory antibody. A polyclonal activator such as PHA (Orion Diagnostics, 2 µg/ml) is usually included as a positive control to check the functionality of the cells and the assay.

The plate is emptied and the cells and appropriate stimuli are transferred to the wells (medium alone is used as control for spontaneously producing cells). For specific stimulation, a cell concentration of 200,000 cells/well is typically used while a lower concentration (e.g. 30,000 cells/well) may be used in wells with polyclonal activators (e.g. PHA or anti-CD3). The plates are incubated either overnight or for two days (may depend on the cytokine analysed) in a 37° C. incubator with 5% $CO_2$.

Development

The cells are discarded and the plates washed with PBS (5×200 µl/well). 100 µl/well of biotinylated anti-cytokine (e.g. anti-IL4 mAb, IL4-II-Biotin, Mabtech) diluted to 1 µg/ml in PBS with 0.5% FCS is added and incubated for about 2 h. The plate is then washed again with PBS (5×200 µl/well) and 100 µl/well Streptavidin-ALP (Mabtech) diluted 1:1000 in PBS with 0.5% FCS is added and incubated for 1 h. The plates are washed with PBS (5×200 µl/well) and developed with BCIP/NBT-Plus substrate (Moss Inc.), filtered through a 0.45 µm membrane. When distinct spots are observed, the development is stopped by washing extensively with tap water. The plates are left to dry and a low-magnifying stereomicroscope (e.g. Nikon, Japan; 40×) or an ELISpot reader (e.g. AID, Germany) is used to view the results.

TABLE 1

ELISpot analysis of IFN-γ producing human PBMC after stimulation with immobilised anti-CD3 antibodies or PHA either immobilised to the membrane or added in solution. Number of cells used was 30,000/well and the time for stimulation was 18 hours.

|  | Number of spots (IFN-γ producing cells) |
| --- | --- |
| No additive | 4 ± 3 |
| Membrane bound anti-CD3 | 414 ± 8 |
| Soluble PHA | 582 ± 63 |
| Membrane bound PHA | 619 ± 68 |

TABLE 2

Specific stimulation of human PBMC with the two antigens PPD and TT in the presence or absence of membrane-bound anti-CD28. The ELISpot was run with 200,000 cells/well and analysed for IL-4 and IL-13 producing cells after 40 hours incubation. The results represent the mean values from triplicates.

|  | No Additive | Anti-CD28 |
| --- | --- | --- |
| IL-4 producing cells |  |  |
| Medium | 3 | 4 |
| PPD | 21 | 83 |
| TT | 30 | 92 |
| IL-13 producing cells |  |  |
| Medium | 0 | 3 |
| PPD | 118 | 240 |
| TT | 19 | 137 |

The invention claimed is:

1. A method of detecting the production of an analyte by cells in a sample, which method comprises:
   (i) contacting an antibody capable of binding to said analyte and a first agent capable of enhancing detection of said analyte with a sample of cells, wherein said antibody and said first agent are immobilised on the same support; and
   (ii) detecting binding of said analyte to said antibody thereby detecting the production of an analyte by cells in a sample.

2. A method according to claim 1, wherein the support is uniformly coated with the antibody and the first agent.

3. A method according to claim 1, wherein the antibody is immobilised at one or more discrete location on said support and the first agent is immobilised either uniformly on the support or at one or more discrete location on said support.

4. A method according to claim 3 wherein two or more different antibodies are immobilised on the support.

5. A method according to claim 1, wherein said cells have been contacted with a second agent capable of stimulating or inhibiting secretion of said analyte.

6. A method according to claim 1, wherein step (i) further comprises contacting said sample of cells with a second agent capable of stimulating or inhibiting secretion of said analyte.

7. A method according to claim 6, wherein said second agent is immobilised on said support.

8. A method according to claim 1, wherein said first agent is capable of enhancing secretion of said analyte.

9. A method according to claim 5, wherein said first agent is capable of potentiating secretion of said analyte in response to said second agent.

10. A method according to claim 8, wherein said first agent is capable of inhibiting an inhibitory signal to enhance secretion of said analyte.

11. A method according to claim 1, wherein said first agent is capable of inhibiting a stimulatory signal to reduce spontaneous secretion of said analyte.

12. A method according to claim 1, wherein at least two different first agents capable of enhancing detection of said analyte are immobilised on said support.

13. A method according to claim 1, wherein said cells are T-cells.

14. A method according to claim 13, wherein said analyte is a cytokine.

15. A method according to claim 13, wherein said first agent is a polyclonal T-cell activator.

16. A method according to claim 15, wherein said polyclonal T-cell activator is a CD3 antibody or a lectin such as PHA or ConA.

17. A method according to claim 13, wherein said first agent is an antibody or recombinant ligand to a costimulatory agent.

18. A method according to claim 17, wherein said costimulatory agent is CD28, ICOS or CD40.

19. A method according to claim 13, wherein said first agent is a cytokine.

20. A method according to claim 19, wherein said cytokine is IL-2, IL-15, IL-4 or IL-12.

21. A method according to claim 13, wherein said first agent is capable of inhibiting an immunostimulatory signal, which signal is IL-10 or TGF-β.

22. A method according to claim 13, wherein said first agent is an extracellular matrix protein.

23. A method according to claim 22, wherein said extracellular matrix protein is fibronectin or laminin.

24. A method according to claim 1, wherein said cells are virus infected cells.

25. A method according to claim 24, wherein said analyte is a viral particle or protein.

26. A method according to claim 24, wherein said virus is HIV, EBV or CMV.

27. A method according to claim 1, wherein said first agent is a viral activator.

28. A method according to claim 24, wherein said viral activator is a CD3 antibody or PHA.

29. A method according to claim 1 which further comprises determining the number of cells which secrete the analyte.

30. An assay plate for use in a method according to claim 1 comprising an antibody specific for an analyte and a first agent capable of enhancing detection of cells secreting said analyte, wherein said antibody and said first agent are immobilised on the same surface.

31. An assay plate according to claim 30, wherein said first agent is capable of enhancing secretion of said analyte.

32. An assay plate according to claim 30, further comprising a second agent capable of stimulating or inhibiting secretion of said analyte is immobilised on said surface.

33. An assay plate according to claim 30, wherein said surface is a PVDF or nitrocellulose membrane.

34. An assay plate according to claim 33 which comprises one or more well, wherein each well has a protein binding capacity of from 50 to 100 micrograms.

35. A kit comprising an assay plate according to claim 30 and a means for detecting binding of said analyte to said antibody.

36. A method of monitoring an immune response, which method comprises:
(i) contacting an antibody capable of binding to a cytokine and a first agent capable of enhancing detection of said cytokine with a sample of cells, wherein said antibody and said first agent are immobilised on the same support; and
(ii) detecting binding of said cytokine to said antibody
thereby monitoring an immune response.

37. A method of diagnosing viral infection, which method comprises:
(i) contacting an antibody capable of binding to a viral particle or protein and a first agent capable of enhancing detection of said viral particle or protein with a sample of cells, wherein said antibody and said first agent are immobilised on the same support; and
(ii) detecting binding of said viral particle or protein to said antibody
thereby diagnosing viral infection.

* * * * *